United States Patent
Steele

(10) Patent No.: US 6,239,122 B1
(45) Date of Patent: May 29, 2001

(54) METHOD OF TREATMENT OF NAUSEA, VOMITING, AND OTHER DISORDERS USING ESTROGENS

(76) Inventor: Joy Ann Steele, 14334 Park Drive, Edmonton Alberta (CA), T5R 5V2

( * ) Notice: Subject to any disclaimer, the term of this patent is extended or adjusted under 35 U.S.C. 154(b) by 0 days.

(21) Appl. No.: 09/478,205

(22) Filed: Jan. 5, 2000

(51) Int. Cl.⁷ ................................................... A61K 31/56
(52) U.S. Cl. ................................................................ 514/179
(58) Field of Search ............................................. 514/182

(56) References Cited

U.S. PATENT DOCUMENTS 5,674,868 * 10/1997 Van Daele et al. .................. 514/260

OTHER PUBLICATIONS

R. Rupprecht & F. Holsboer, Neuroactive Steroids: Mechanisms of Action and Neuropsycho Pharmacological Perspectives Trends in Neuroscience (1999) 22:410–416.

C.H.R. Wetzel et al. Functional Antagonism of Gonadal Steroids at the 5–Hydroxytrptamine Type 3 Receptor. Molecular Endocrinology (1998) 12:1441–1451.

J.A. Steele & I.L. Martin, Interaction of Oestrone and 17β–Oestradiol with the 5–HT₃Receptor. British Journal of Pharmacology, Proceedings Supplement (1999) 126:15P.

* cited by examiner

*Primary Examiner*—Theodore J. Criares
*Assistant Examiner*—Jennifer Kim

(57) ABSTRACT

The use of estrone or derivatives of estrone, equilin, or equilenin, including pharmaceutically acceptable salts, as well as pharmaceutical compositions comprising these compounds as a therapeutic agent in humans or in animals is claimed. The asserted use is as an antiemetic agent or for the treatment of other disorders that can be ameliorated by noncompetitive antagonism of the 5-hydroxytryptamine type 3 receptor.

21 Claims, No Drawings

METHOD OF TREATMENT OF NAUSEA, VOMITING, AND OTHER DISORDERS USING ESTROGENS

CROSS-REFERENCE TO RELATED APPLICATIONS

Not applicable.

STATEMENT REGARDING FEDERALLY SPONSERED RESEARCH OR DEVELOPMENT

Not applicable.

REFERENCE TO A MICROFICHE APPENDIX

Not applicable.

BACKGROUND OF THE INVENTION

1. Field of the Invention

A new use for estrone, derivatives of estrone, equilin and equilenin, including pharmaceutically acceptable salts, as well as pharmaceutical compositions containing these compounds is claimed.

2. Description of Related Art

Basic Science Prior Art

The 5-$HT_3$ receptor is a ligand-gated ion channel

The 5-hydroxytryptamine type 3 receptor (5-$HT_3$ receptor) is a member of the ligand-gated ion channel superfamily of proteins (Jackson, M. B. & Yakel, J. L., 1995, Ann. Rev. Physiol. 57:447–468). Ligand-gated ion channels are transmembrane proteins. They appear to be composed of five subunits assembled around a central channel that forms a pathway for ions. Binding of an agonist leads to the opening of the gate of the ion channel to allow movement of ions across the cell membrane. The natural agonist is serotonin (5-hydroxytryptamine, 5-HT). Two subunits of the 5-$HT_3$ receptor have been cloned to date (Maricq, A. V., Peterson, A. S., Brake, F. J., Myers, R. M. & Julius, D., 1991, Science, 254:432–437; Davies, P. A., Pistis, M., Hanna, M. C., Peters, J. A., Lambert, J. J., Hales, T. G. & Kirkness, E. F., 1999, Nature 397:359–363). Several immortal cell lines express high densities of 5-$HT_3$ receptors including the cell line that I used in my experiments (NCB-20). The cDNA cloned from the NCB-20 cell line is nearly identical (98% identity) to the cDNA cloned from humans (Maricq et al., 1991).

Steroids act on ligand-gated ion channels

The importance of steroids as crucial components of cellular membranes is well established. Equally well established are the long term endocrine effects of steroid hormones. These endocrine effects result from the binding of steroids to intracellular receptors that subsequently interact with DNA and modulate gene expression. Less well delineated, but currently the subject of increasing interest, are the immediate modulatory effects of certain steroids on ligand-gated ion channels (Rupprecht, R. & Holsboer, F., 1999, TINS 22(9):410–416). For example, it is now established that steroid anesthetics, as well as certain endogenous metabolic products of progesterone and deoxycorticosterone, act on the gamma-aminobutyric acid type A receptor ($GABA_A$ receptor) at extremely low concentrations. The $GABA_A$ receptor belongs to the same family of proteins as the 5-$HT_3$ receptor. However, most of the reported effects of steroids on ligand-gated ion channels occur at high micromolar concentrations and it is not clear that these effects have any physiological relevance or hold any potential for a therapeutic action. These nonspecific effects may result from the lipophilic nature of steroids. Although steroids have long been used as therapeutic agents for endocrine indications, no steroid is currently on the market as an agent that targets a ligand-gated ion channel. Alphaxalone, a steroid anesthetic that targeted the $GABA_A$ receptor, is the only example and it was withdrawn from the market because of problems with the pharmaceutical carrier.

Estrogens are steroids

Estrogens belong to a class of steroids that are responsible for the development of female secondary sexual characteristics as well as the differentiation, growth and functioning of many tissues in the male. Estrogens also play an important role in the establishment and maintenance of pregnancy. The three most abundant estrogens in humans are estradiol, estrone and estriol. Of the these three, estradiol is the most potent and is the major secretory product of the ovary. Estrogens are extensively metabolized. For example, estradiol administered orally to humans is metabolized to estrone by the gastrointestinal mucosa and the liver (Lievertz, R. W., 1987, Am. J. Obstet. Gynecol. 156:1289–1293). During pregnancy, estrogens are synthesized by the placenta in large quantities (De Hertogh, R. et al., 1975, J. Clin. Endocrinol. Metab. 40:93–101).

Estradiol is an antagonist of the 5-$HT_3$ receptor at high concentrations

I have found that estradiol antagonizes the 5-$HT_3$ receptor at high concentrations. The concentration of estradiol needed to inhibit the functioning of the 5-$HT_3$ receptor by 50% ($IC_{50}$) was about 3 $\mu$M. This observation was presented in 1994 at the International Union of Pharmacologists (IUPHAR) meeting. This observation has also been published by another group (Wetzel, C. H. R., et al., 1998, Mol. Endocrinol. 12(9):1441–1451). Unfortunately, because such high concentrations of estradiol were needed to cause an effect, the action on the 5-$HT_3$ receptor is not of any physiological relevance. Normally, the plasma concentrations of estrogens are in the picomolar range. Only during the condition of pregnancy does the plasma level of estrogens rise into the low nanomolar range (De Hertogh, et al., 1975). This low affinity binding site for estradiol on the 5-$HT_3$ receptor is also not useful as a therapeutic target since unreasonably high concentrations of estradiol would have to be administered to a human to exert an effect on the 5-$HT_3$ receptor.

The presence of a low affinity binding site on the 5-$HT_3$ receptor for a steroid is predictable from the prior art because many different ligand-gated ion channels as well as G-protein coupled receptors have low affinity binding sites for steroids (Rupprecht & Holsboer, 1999). Since only a few high affinity binding sites have been found, it is not necessarily predictable that the 5-$HT_3$ receptor would have a high affinity binding site. More importantly, it is certainly not possible to predict the identity of a steroid which would have a high affinity for a receptor. This is because the existence of a high affinity binding site must first be established and then the structure-activity properties of the binding site must be elucidated. As detailed later in this specification, I surprisingly discovered a high affinity binding site on the 5-$HT_3$ receptor for estrone. This site is potentially useful as a therapeutic target for the treatment of nausea and/or vomiting and perhaps other, as yet unidentified therapeutic indications. The reason that this site is of potential therapeutic value is that only very low amounts of an estrogen would need to be administered to a human to acheive a therapeutic effect through an action on the 5-$HT_3$ receptor. The 5-$HT_3$ receptor is involved in the control of vomiting in human and in animals 5-HT$_3$ receptors are widely distributed in the mammalian central, peripheral and enteric nervous systems and have also been found on cells of the immune system. The enteric nervous system resides within the walls of the gastrointestinal tract. 5-HT$_3$ receptors have been found to play an important role in the control of vomiting in a variety of mammals including humans (Veyrat-Follet, C., Farinott, R. & Palmer, J. L., 1997, Drugs 53(2):206–234). The receptors are present in the part of the brain that is involved in controlling vomiting as well as in the gastrointestinal tract. Receptors at both locations have been shown to be involved in vomiting. It is thought that 5-HT released from the enterochromaffin cells of the gastrointestinal mucosa acts on 5-HT$_3$ receptors to initiate the vomiting reflex. Chemotherapy and radiotherapy, two important clinical causes of vomiting, may cause release of 5-HT from the enterochromaffin cells. Chemotherapeutic agents also appear to act directly on the chemoreceptor trigger zone of the vomiting center in the brain that then feeds onto neurons containing 5-HT$_3$ receptors to initiate vomiting.

Currently unidentified physiological roles of 5-HT$_3$ receptors

It is only relatively recently that 5-HT$_3$ receptors were identified. The only well described physiological role for these receptors is that of the control of vomiting as described above. However, since the receptors are so widely distributed throughout the central nervous system, including numerous regions of the brain, it is likely that further research will identify additional physiological roles for these receptors. Importantly for the scope of the invention described in this specification, it is likely that 5-HT$_3$ receptors may also be found to be involved in the etiology of various disorders or diseases. For example, it has been shown that 5-HT$_3$ receptor antagonists display anxiolytic (Rodgers, R. J., Cole, J C. & Tredwell, J. M., 1995, Psychopharmacology 117:306–312) and atypical antipsychotic properties (Zoldan, J., Friedberg, G., Goldberg-Stem, H. & Melamed, E., 1993, Lancet 341:562–563).

CLINICAL SCIENCES BACKGROUND

"Nausea and/or vomiting"

Nausea and vomiting are separate symptoms. Nausea is a feeling of distress and is often accompanied by the urge to vomit. Nausea can frequently occur without vomiting. Vomiting is the reflex act of disgorging the contents of the stomach through the mouth and is generally preceded by nausea. However, vomiting generally occurs with nausea and thus is commonly referred to as nausea and vomiting. Vomiting is also called emesis. Pharmaceutical agents that are employed to treat vomiting are referred to as antiemetic agents. However, since nausea usually precedes emesis, antiemetic agents can, but not necessarily, ameliorate the sensation of nausea. The phrase "nausea and/or vomiting" is used throughout the specification and the claims and is intended to mean the symptoms of nausea or vomiting occurring together or separately.

Nausea and/or vomiting as a clinical problem

Nausea and/or vomiting are unpleasant and at times limiting side-effects in several clinical areas. These symptoms are frequently experienced following the administration of chemotherapeutic agents used in the treatment of cancer and other diseases. The symptoms caused by the chemotherapeutic agents may be so severe that the patients may refuse further treatment. Examples of chemotherapeutic agents for which nausea and/or vomiting are side-effects include cisplatin, cyclophosphamide, carboplatin and others. The ability of chemotherapeutic agent to induce emesis varies with the agent and ranges from high to low. When used in combination, the emetogenic potential of each agent is additive. Cisplatin has the highest emetogenic potential of any chemotherapeutic agent. It has also become apparent that chemotherapeutic agents cause two distinct phases of nausea and/or vomiting. The first phase occurs shortly after the administration of the chemotherapeutic agent and begins to subside by 12 to 24 hours. This phase is called acute nausea and/or vomiting. A second phase of nausea and/or vomiting that develops 24 hours after chemotherapy is called delayed nausea and/or vomiting. About 1 in 9 patients experience delayed nausea and/or vomiting and thus this is a significant clinical problem (Morrow, G. R., Hickok, J. T., Burish, T. G. & Rosenthal, S. N., 1996, Am. J. Clin. Oncol. 19(2):199–203).

The radiotherapy used to treat cancer and other diseases can also cause nausea and/or vomiting.

The occurence of radiotherapy-induced nausea and/or vomiting is dependent on several factors including site, field size and dose per fraction. Clinical considerations also include prior surgery and exposure to chemotherapy. Vomiting is more likely to occur when radiotherapy is applied to the upper abdomin, when the field size is large and when the dose per fraction is high.

Post-operative nausea and/or vomiting induced by the use of general anesthetics is also a clinical problem. The incidence of symptoms also depends on the site with abdominal, gynecological, ear, eye, nose and throat surgeries having the highest incidence.

Current solutions to the clinical problem of nausea and/or vomiting

There are nine groups of agents that are used clinically for the treatment of emesis. The nine groups are: anticholinergics, antihistamines, phenothiazines, butyrophenones, cannabinoids, benzamides, glucocorticoids, benzodiazepines and 5-HT$_3$ receptor competitve antagonists (Merck Manuel, 1992, Merck Research Laboratories). In general, there are several agents in each group.

Competitive antagonists of the 5-HT$_3$ receptor are used clinically as antiemetic agents The introduction of 5-HT$_3$ receptor competitive antagonists into clinical practice revolutionized the treatment of emesis because these agents are more efficacious and have fewer side-effects than antiemetic agents from the other groups (Markham, A. & Sorkin, E. M., 1993, Drugs, 45:931–952). These agents are: ondansetron (Zofran™, GlaxoWelcome), granisetron (Kytril™, SmithKline Beecham) and tropisetron (Navoban™, Sandoz). At the present time, the 5-HT$_3$ competitive antagonists in combination with the corticosteroid dexamethasone represent the best prophylaxis and treatment of acute nausea and/or vomiting.

Disadvantages of Present Antiemetic Agents

Drugs that act at sites other than the 5-HT$_3$ receptor are not very efficacious and have poor side effect profiles. For example, metoclopramide, a benzamide, that acts at dopamine as well as 5-HT receptors exhibits serious and undesirable side-effects such as extra-pyramidal effects characterized by tardive dykinesia, acute dystonias, akathisia and tremor. Another example is chlorpromazine, a phenothiazine, which not only has extra-pyramidal side-effects but cognitive effects as well. Dexamethasone, a glucocorticoid, is the only steroid used as an antiemetic agent. It is not very efficacious and is not generally employed as a single agent. It is often used in combination with 5-HT$_3$ receptor competitive antagonists for the prevention of emesis in the highly emetogenic therapeutic regimes.

Dexamethasone has several unpleasant side-effects such as insomnia, dysphoria, fluid retention and muscle weakness. The site of action for dexamethasone inducing an antiemetic effect is unknown.

Limitations of the 5-$HT_3$ receptor competitive antagonists as antiemetic agents Despite the tremendous advance in the management of emesis with the intoduction of the 5-$HT_3$ receptor competitive antagonists, there is still lots of room for improvement (Morrow, G. R., Hickok, J. T. & Roenthal, S. N., 1995, Cancer 76(3):343–357). These agents have been found to be ineffective in 40 to 60% of patients. Efficacy appears to be more pronounced for cisplatin-containing regimes than for moderate or less emetogenic chemotherapy regimes. Effectiveness also appears to be less for delayed nausea and emesis than for acute symptoms. Control over nausea appears to be significantly less than control over emesis with control over nausea remaining incomplete in approximately half of the patients. As well, the efficacy of the agents appears to diminish across repeated days and across repeated chemotherapy cycles. Interestingly, the addition of dexamethasone increases the efficacy of both the 5-$HT_3$ receptor competitive antagonists and other antiemetic agents. Taken altogether, there is still a need for a safe and efficacious antiemetic agent.

In addition, 5-$HT_3$ receptor competitive antagonists are extremely expensive. Consequently, they are not prescribed to the extent that they are needed and the cost of these agents is a burden to the health care system.

Estrone is an old drug and is also an endogenous hormone in both women and men.

Estrone has been in clinical usage for gynecological (endocrine) indications for several decades. Estrone has an excellent side effect profile. No adverse events have been reported to the Food and Drug Administration's Adverse Event Reporting System (AERS) as of October 1999. Pregnant women have a plasma level of up to 30 nM of unconjugated estrone during the last six months of pregnancy (De Hertogh, D., Thomas, K., Bietlot, Y., Vanderheyden, I. & Ferin, J., 1975, J. Clin. Endocrinol. Metab. 40:93–101) without any obvious ill effects. This plasma level is about three times the level expected to be needed for estrone to exert a therapeutic effect as an antiemetic agent as claimed in this invention. Consequently, no adverse side-effects are anticipated. Unconjugated estrone is also present in men at a plasma concentration of 90 to 330 pM.

Estrone as the sole active ingredient has been available as a preparation for intramuscular injection (Theelin™ and others) and as a vaginal cream. Estrone is also a component of the preparations prescribed for hormone replacement therapy in the treatment of menopause (Premarin™). Premarin also contains several other estrogens: delta-8-estrone, equilin and equilenin (Bhavnahi, B. R., 1998, Proc. Soc. Exp. Biol. Med. 217:6–16).

BRIEF SUMMARY OF THE INVENTION

This invention discloses a new use for estrone or derivatives of estrone, equilin, and equilenin. The asserted use is an antiemetic agent or for the treatment of other disorders that can be ameliorated by noncompetitive antagonism of the 5-hydroxytryptamine type 3 receptor (5-$HT_3$ receptor). Emesis is defined as vomiting and an antiemetic agent is a therapeutic agent which prevents or relieves the symptoms of vomiting. Estrone would be administered to a human or an animal in need of antiemetic therapy as the active ingredient in a pharmaceutical composition. There is still a clinical need for antiemetic agents that are effective and devoid of undesirable side-effects. I collected in vitro data that demonstrated that estrone noncompetitively antagonized the functioning of a 5-$HT_3$ receptor at very low nanomolar concentrations. That is, I discovered a high affinity steroid binding site on the 5-$HT_3$ receptor. This information had not been previously described and cannot be deduced from the prior art. My assertion that estrone can act as an antiemetic agent in mammals, including humans, is based on the following correlations. Since antagonists of the 5-$HT_3$ receptor are efficacious antiemetic agents in humans and in animals, and since estrone is an antagonist of the 5-$HT_3$ receptor, estrone should also serve as an antiemetic agent. In addition, estrone appears to be a natural, endogenous antiemetic in humans being responsible for the cessation of pregnancy-induced nausea and vomiting. Further experiments revealed that the oxygen at carbon 17 of the steroid structure is required for a high affinity interaction with the receptor. Consequently, the use of the closely related estrogens with an oxygen at carbon 17, equilin and equilenin is also claimed.

BRIEF DESCRIPTION OF THE SEVERAL VIEWS OF THE DRAWING

Not applicable.

DETAILED DESCRIPTION OF THE INVENTION

Estrone has been in clinical usage for decades. Many aspects of its use in humans such as safety, side-effects, routes of administration, pharmacokinetics and biological actions are known. Estrone is currently not being used as an antiemetic agent. It is in clinical usage for gynecological (endocrine) indications only. There are nine groups of agents that are used as antiemetic agents. Estrone can be distinguished from eight of these groups by the fact that it acts on the 5-$HT_3$ receptor while the other eight groups act at other receptors such as dopamine receptors. The remaining group of antiemetic agents act at the 5-$HT_3$ receptor by competitive antagonism of the agonist binding site. Estrone can be distinguished from these agents since it acts at the 5-$HT_3$ receptor but by a noncompetitive mechanism.

Advantages of estrone over other groups of antiemetic agents

Competitive antagonists of the 5-$HT_3$ receptor have been found to be the most efficacious antiemetic agents. Most of the antiemetic agents in clinical use do not act at the 5-$HT_3$ receptor. Since I have surprising found that estrone is a very potent antagonist of the 5-$HT_3$ receptor, I anticipate that estrone will be more efficacious than any of the agents that act at sites other than the 5-$HT_3$ receptor. Also, estrone has been in clinical usage for decades for endocrine indications. It has been found to be safe and virtually free of untoward side-effects. All of the antiemetic agents that act at sites other than the 5-$HT_3$ receptor have very unpleasant side-effects. For example, metoclopramide induces undesirable problems with movement such as dystonias. Antihistamines cause problems with sedation and anticholinergic agents cause anticholinergic side-effects. Estrone will not induce problems with dystonias, sedation or anticholinergic effects.

Advantages of estrone over the 5-$HT_3$ receptor competitive antagonists

Estrone has an advantage over the 5-$HT_3$ receptor competitive antagonists as its biological half-life is about 4 times longer: 12 to 14 hours compared to 3 to 4 hours (Compendium of Pharmaceuticals and Specialties, latest edition; Lievertz, R. W., 1987, Am. J. Obstet. Gynecol. 156:1289–1293). Also, there are additional routes of administration available: sublingual, transdermal patch and intramuscular injection. Administration by a transdermal patch would be particulary useful in preventing the emesis caused by radiotherapy since these treatments are generally given over an extended period of time. Estrone is a natural compound and is very inexpensive. The retail price is about 2% that of ondansetron. For a rough price comparison, ondansetron sells for about $20 per tablet. Tablets containing estrogens sell for about $0.20 per tablet or 1% of ondansetron tablets. Consequently, the use of estrone as an antiemetic agent would result in significant savings to the health care system. The more efficacious 5-HT$_3$ receptor competitve antagonists are not used as much as they are needed owing to their cost. Consequently, a less expensive, efficacious antiemetic agent such as estrone is needed.

Disadvantages to the use of estrone as an antiemetic agent

Estrone would be contraindicated in most estrogen-dependent cancers except those that have reached the stage of palliative treatment. Based on the incidence of various cancers, this would represent about 10% of the market. Since this is a clearly defined contraindication, it is not a very large disadvantage. Estrone would also be strictly contraindicated in the first trimester of pregnancy according to the guidelines of the Food and Drug Administration.

Experimental Data

Estrone is a noncompetitive antagonist of the 5-HT$_3$ receptor at low nanomolar concentrations I surprisingly discovered that a steroid hormone, estrone, antagonises the 5-HT$_3$ receptor at extremely low nanomolar concentrations. This action of estrone was previously unknown and cannot be predicted from the prior art. This observation demonstrates that a high affinity binding site for steroids exists on the 5-HT$_3$ receptor.

I used NCB-20 cells (mouse neuroblastoma×Chinese hamster brain cell line), an immortal cell line that expresses 5-HT$_3$ receptors at a high density. Cells were grown in Dulbecco's modified Eagles medium containing 10% fetal bovine serum, 100 U/ml penicillin, 100 μg/ml streptomycin and 2 mM glutamine. Cells were incubated in 35 mm plates at 37 degrees C in a humidified 7% carbon dioxide atmosphere. An earlier patch clamp study of NCB-20 cells showed that the currents elicited by 5-HT are exclusively carried by 5-HT$_3$ receptors (Lambert, J. J., Peters, J. A., Hales, T. G. & Dempster, J., 1989, Br. J. Pharmacol. 97:27–40). I recorded membrane currents carried by 5-HT$_3$ receptors under voltage-clamp from single cells using the whole-cell configuration of the patch clamp technique (Hamill, O. P., Marty, A., Neher, E., Sakmann, B. & Sakmann, F. J., 1981, Pfluegers Arch. 391:85–100). Recordings were performed at a holding potential of −60 mV. Ligands were applied to the cells using a gravity-feed rapid perfusion system.

Estrone antagonizes the open conformation of the 5-HT$_3$ receptor at low nanomolar concentrations Application of a low concentration of 5-HT (0.5 μM) elicited an inward current that did not decline (desensitize). When the agonist is bound to the receptor and the receptor is conducting current, the receptor is in an open conformation. Co-application of estrone with 5-HT (0.5 μM) showed that estrone rapidly and reversibly blocked the current at low nanomolar concentrations. That is, estrone antagonized the open conformation of the receptor. Consequently, the open conformation has a high affinity binding site for estrone. Concentration-effect data from 21 cells were fitted with the Hill (logistic) equation. The concentration of estrone that inhibited 50% of the current (IC$_{50}$) was found to be 1.5 nM with the standard error of the mean being 0.2 nM (Steele, J. A & Martin, I. L., 1999, Brit. J. Pharm. 126:Proc. Sup.).

Structure-activity information for the high affinity binding site: a ketone group at the carbon 17 position is crucial Comparison of data from three estrogens: estrone, estradiol and estriol gave some structure-activity information. Using the co-application protocol described above, the IC$_{50}$ for estradiol was found to be 81±12 nM (10 cells). Estradiol has a hydroxyl group at the carbon 17 position on the D ring of the steroid nucleus while estrone has a ketone group. Since this is the only difference between the two molecules, it is clear that a ketone group at the carbon 17 position is crucial for a high affinity interaction. The IC$_{50}$ for estriol was found to be 22±8 μM (8 cells). Estriol has hydroxyl groups at carbons 16 and 17 and is essentially devoid of activity. Therefore, a steroid compound with a ketone group at the carbon 17 position is needed for activity. Several closely related compounds to estrone which have a ketone at the carbon 17 position are equilin and equilenin. These two compounds are estrogens extracted from pregnant mares' urine and are contained in the prescription drug Premarin ™ (Wyeth-Ayerst). Based on the data to date, equilin, equilenin, 2-OH-estrone, 4-OH-estrone, and delta-8-estrone should be active at the 5-HT$_3$ receptor since they all possess the basic steroid nucleus of an estrogen with a ketone group at the carbon 17 position.

Estrone antagonizes the 5-HT$_3$ receptor by a noncompetitive mechanism

The block by estrone was found not to be competitive with the agonist 5-HT. The EC$_{50}$ (concentration of 5-HT at which 50% of maximum current amplitude was elicited) for 5-HT was 2.2±0.2 μM in the absence of estrone (8 cells) and 4.2±0.3 μM in the presence of estrone (8 cells). A noncompetitive antagonist does not shift the EC$_{50}$ for the agonist as is the case with estrone. It appears that estrone antagonizes the 5-HT$_3$ receptor through an allosteric mechanism and thus differs in its mechanism of block from ondansetron, granisetron, and tropisetron which are competitive antagonists.

The above data that shows that there is a high affinity binding site on the 5-HT$_3$ receptor which had not been previously known. A low affinity binding site for estradiol has been reported (Wetzel et al., 1998) as described in the Background section. I also found a low affinity binding site for estradiol with an IC$_{50}$ of 3.1±0.02 μM (8 cells) and a low affinity site for estrone with an IC$_{50}$ of 0.3±0.02 μM (15 cells). These blocking sites were revealed by applying the estrogens before the 5-HT (10 μM) was applied. The estrogens were then interacting with the agonist-free non-conducting state of the receptor. This is also called the closed conformation of the receptor. Consequently, it is only when the receptor is in the agonist-bound, conducting state that the high affinity binding site is available. Conformation-dependent binding site affinities for ion channels are well known (Hille, B., 1992, Ionic Channels of Excitable Membranes, Sinauer Assoc. Inc., pp. 390–422). However, it could not be predicted that such a high affinity binding site would be present on the 5-HT$_3$ receptor. This was an unexpected discovery. It is important to point out that it is the high affinity binding site that enables this disclosed invention to be useful. It is this site that can be a target for a therapeutic agent. This is because only a small amount of an estrogen would have to be administered to achieve a high enough concentration in the plasma to be therapeutically effective.

Suggested biological activity based on the in vitro experimental data: Estrone exhibits antiemetic activity The asserted utility of estrone or derivatives of estrone as well as equilin and equilenin as an antiemetic agents in mammals including humans is based on two correlations. First, antagonists of the 5-$HT_3$ receptor such as ondansetron are in clinical usage as antiemetic agents. Therefore, since estrone also antagonizes the 5-$HT_3$ receptor, it should also act as an antiemetic agent. Second, estrone appears to be an endogenous antiemetic in humans. I suggest that estrone plays an important physiological role in the cessation of pregnancy-induced emesis ('morning sickness'). The plasma levels of free, unconjugated estrone are low during the first trimester of pregnancy when at least 50% of women experience nausea and vomiting (Klebanoff, M. A., Koslowe, P. A., Kaslow, R. & Rhoads, G. G., 1985, Obstet. Gynecol. 66:612–616). The plasma level of estrone rises dramatically at the end of the first trimester as a result of increased synthesis by the placenta (De Hertogh et al., 1975). This dramatic rise in the levels of estrone corresponds to the time of the cessation of morning sickness. The mean concentration of estrone at this time during pregnancy (12 weeks) was found to be 3.7 nM which is about the same as the $IC_{50}$ (1.5 nM) that I measured in the in vitro preparation. This extremely close correlation suggests that estrone is responsible for resolving the nausea and/or vomiting induced by pregnancy.

Contemplated Modes of Use

My discovery of a high affinity binding site for estrogens on the 5-$HT_3$ receptor which is distinct from the agonist site, is the novel aspect of this invention. Consequently, any ligand that is capable of noncompetitively antagonizing the 5-$HT_3$ receptor with an $IC_{50}$ value less than 75 nM is meant to be included within the scope of this invention. Based on the data collected to date, a compound selected from a group comprising estrone, 2-OH-estrone, 4-OH-estrone, delta-8-estrone, an obvious chemical derivative of estrone, equilin and equilenin could be used as a therapeutic agent in humans or in animals. It is intended to be understood that the compound must be formulated into a pharmaceutical composition appropriate to the route of administration for administration to a human or an animal. Currently, the only well described therapeutic use for an antagonist of the 5-$HT_3$ receptor is that of an antiemetic agent. However, it is likely that additional therapeutic uses for 5-$HT_3$ antagonists will be identified. Consequently, any disease or disorder that may be treated with a 5-$HT_3$ receptor noncompetitive antagonist is meant to be included within the scope of the present invention.

Currently identified therapeutic indications for a 5-$HT_3$ antagonist

5-$HT_3$ receptor antagonists are currently used as antiemetic agents. Thus, a method of treatment to prevent or to provide relief from nausea and/or vomiting by administering a 5-$HT_3$ receptor noncompetitive antagonist to a human or an animal is claimed. Nausea and/or vomiting occurs as a clinical problem as a result of administration of chemotherapeutic agents to treat cancer or other diseases. It also occurs as a result of radiotherapy to treat cancer or other diseases. In addition, general anesthetic agents used during surgery cause nausea and/or vomiting.

Currently unidentified therapeutic indications for a 5-$HT_3$ receptor noncompetitive antagonist The physiological roles of the 5-$HT_3$ receptors have not been exhaustively described. It is likely that further research will uncover additional physiological roles for this receptor. Consequently, it is also likely that 5-$HT_3$ receptors may be found to involved in the etiology of disorders or diseases other than those that involve vomiting. Since 5-$HT_3$ receptors are located in the central, peripheral and enteric nervous systems, and cells of the immune system (Khan, N. A. & Poisson, J. P., 1999, J. Neuroimmunol. 99(1):53–60), it is likely that the disorders or diseases will involve these systems specifically. It is also possible that the symptoms of these disorders or diseases may be ameliorated by noncompetitively antagonizing the functioning of 5-$HT_3$ receptors. For example, it has been suggested that 5-$HT_3$ receptor antagonists may be useful in treating various behavioral disorders (Apud, J. A., 1993, Neuropsychopharmacology 8:117–130). These antagonists have shown some anxiolytic (Rodgers, R. J., Cole, J. C. & Tredwell, J. M., 1995, Psychopharmacology 117:306–312) and atypical antipsychotic properties (Zoldan, J., Friedberg, G., Goldberg-Stern, H. & Melamed, E., 1993, Lancet 341:562–563). It is intended that these currently unidentified therapeutic indications be included within the scope of the claims of this invention.

The term "disorder" means an abnormal physical or mental condition that includes but is not limited to disorders of gastrointestinal motility, as well as mood, thought, and behavioral disorders. The symptoms include but are not limited to diarrhea and related symptoms such as decreased absorption times, depressed moods, cognitive problems such as mental slowing, problems with attention such as inability to concentrate and headache.

Active ingredient

The term active ingredient means one of the named compounds or its pharmaceutically acceptable salt. Estrone, delta-8-estrone, 2-OH-estrone, 4-OH-estrone, equilin and equilenin are commercially available. Pharmaceutically acceptable salts of these compounds can be formed according to conventional means known in the art. Estrone, equilin, equilenin, and delta-8-estrone are contained in the currently available prescription drug Premarin™ (Bhavnani, B., 1998, Proc. Soc. Exp. Biol & Med. 217:6–16).

The systematic names of the named compounds are:
Estrone is 3-hydroxyestra- 1,3,5(10)-trien- 17-one.
Estradiol is estra-1,3,5(10)-triene-3,17B-diol.
Delta-8-estrone is 3-hydroxyestra- 1,3,5(10),8-tetraen-17-one.
4-OH estrone is 4-hydroxyestra-1,3,5(10)-trien-17-one.
2-OH estrone is 2-hydroxyestra-1,3,5(10)-trien-17-one.
Equilin is 3-hydroxyestra- 1,3,5(10),7-tetraen- 17-one.
Equilenin is 3-hydroxyestra-1,3,5,7,9-pentaen-17-one.

A "chemical derivative" of estrone according to the invention is a compound which exhibits a chemical difference but is a noncompetitive antagonist of the 5-$HT_3$ receptor with an $IC_{50}$ value less than 75 nM. Such a compound must also demonstrate a tolerable side-effect profile when administered to a human or an animal at a dose sufficient to provide relief from symptoms. Some chemical derivatives of estrone are 4-OH estrone, 2-OH estrone, and delta-8-estrone. Other chemical derivatives of estrone can be prepared using standard chemical methodology. For example, halogenation of the rings of the steroid structure have been found to provide useful therapeutic agents. The rings can be halogenated at various positions with chlorine, fluorine, iodine or bromine atoms. For example, clomestrone (16-chloro-3-methoxyestra-1,3,5-(10)-trien-17-one) is chlorinated at the carbon 16 position. This compound was previously used as a therapeutic agent.

A "pharmaceutically acceptable salt" of the active ingredient according to the invention is understood to mean both inorganic and organic salts, such as described in Remington's Pharmaceutical Sciences (latest edition). Although the free-base forms of the compounds can be used in the methods of the present invention, it may be preferred to prepare and use a pharmaceutically acceptable salt form. The compounds named in this invention form pharmaceutically acceptable acid and base addition salts with a wide variety of inorganic, and preferably, organic salts and include the physiologically acceptable salts that are often used in pharmaceutical chemistry. Such salts are also part of this invention. Typical inorganic salts used to form such salts include hydrochloric, hydrobromic, nitric, sulfuric and the like. Salts derived from organic acids may also be used. Such pharmaceutically acceptable salts include but are not limited to acetate, benzoate, citrate, cypionate, enanthate, undecylate, valerate, maleate, proprionate, deconate, sulfate, sulfonate, fumarate, glucoronate and salts with physiologically tolerable amines. These salts can be prepared as esters of the estrogens according to conventional methods known to a person skilled in the art. The salts of the esters of estrogens are often referred to as conjugated estrogens. Conjugated estrogens may be derived wholly or in part from equine urine or may be prepared synthetically. A pharmaceutically acceptable salt of estrone additionally includes estropipate which is also referred to as piperazine estrone sulfate. Estropipate is contained in the pharmaceutical composition Ogen™ (Pharmacia & Upjohn) which is prescribed for hormone replacement therapy in the treatment of menopausal symptoms. Consequently, the active ingredient according to the invention may be a compound other than estrone.

A "metabolic precursor" of estrone is defined as any compound administered to a human or an animal that is metabolized to estrone. For example, it is known that estradiol when orally administered to a human is metabolized to estrone by the gastrointestinal mucosa and the liver (Lievertz, R. W., 1987, Am. J. Obstet. Gynecol. 156:1289–1293).

It is meant to be understood that any of the possible stereoisomers of the compound that is selected as the active ingredient is included within the scope of the invention. A stereoisomer is a compound in which the atoms are linked in the same order but differ in their spatial arrangements. For example, estrone has chiral centers and therefore can exist in numerous stereoisomeric forms. For purposes of this invention, the name of the compound is meant to include all stereoisomeric forms of the compound. The compound could be used in a pure form or as a mixture of stereoisomers. Stereoisomers can generally be prepared following procedures known in the art.

Pharmaceutical compositions containing the active ingredient

The term "pharmaceutical composition" means combining the active ingredient or a pharmaceutically acceptable salt with one or more pharmaceutically acceptable carriers, diluents or excipients to form a pharmaceutical formulation or preparation suitable for administration to a human or an animal. A pharmaceutical composition can be prepared by procedures known in the art using well known and readily available ingredients. The pharmaceutical composition will vary according to the route of administration, e.g. intramuscular, intravenous, oral, transdermal, sublingual, etc. Standard methods of formulating compounds for administration as pharmaceuticals can be found in Remington's Pharmaceutical Sciences, Mack Publishing Company, Easton, Pa., latest edition.

The term "pharmaceutically acceptable" means that the carriers, diluents, excipients and/or salts must be compatible with the other ingredients of the composition, and not deleterious to the recipient.

Non-parenteral administration

Oral

For oral administration, the active ingredient is generally administered as a tablet, capsule, or syrup and pharmaceutically acceptable nontoxic compositions are formed using the normally employed excipients auch as pharmaceutical grades of mannitol, lactose, starch, magnesium stearate, talcum, cellulose, magnesium carbonate, and so forth. The active ingredient may also be micronized in a fluid energy mill to decrease the particle size. It has been found that preparing estradiol in a micronized form increases its absorption from the gastrointestinal tract and this is likely to hold true for the compounds named in the methods of the present invention.

Sublingual

For sublingual administration, the active ingredient is generally administered as a tablet and pharmaceutically acceptable compositions are formed as detailed above for oral administration.

Suppositories

For administration via suppository, conventional binders and carriers include, for example, polyalkylene glycols or triglycerides, and the suppositories generally contain active ingredient in the range of 0.5 to 10%.

Parenteral

Parenteral administration refers to any route that does not involve the intestinal tract and is characterized by injection, whether subcutaneously, intramuscularly, or intravenously, by transdermal delivery via a patch, or by implantation of subcutaneous pellets.

Injection

Injectables can be prepared in conventional forms, either as solutions or suspensions, in solid forms suitable for solution or suspension in liquid prior to injections or as emulsions. Suitable excipients include water, saline, dextrose, glycerol, and the like. If desired, the pharmaceutical compositions may also include minor amounts of nontoxic auxiliary substances, such as wetting agents or emulsifying agents, pH-buffering agents and so forth. Estrone has been available as a prescription drug over the past several decades in a pharmaceutical composition for intramuscular injection, for example, Theelin™ (Parkedale) and many others.

Transdermal delivery

A transdermal patch may be used to deliver the active ingredient in accordance with known techniques. The patch is typically applied for a long period, e.g. 1 to 4 days, allowing a slow and constant delivery of the active ingredient. This may be a preferred route of administration when nausea and vomiting is induced by radiotherapy. Radiotherapy for the treatment of cancer or other diseases is generally given over the course of days to weeks and the constant supply of an antiemetic agent by a transdermal patch would be a convenient method of treatment. In a transdermal patch, the patch itself maintains the active ingredient in contact with the desired localized skin surface. A solvent system for a transdermal patch may include, for example, oleic acid, linear alcohol lactate and dipropylene glycol, or other solvent systems known in the art. The active ingredient may be dissolved or suspended in the carrier.

Determination of dose

The term "effective amount" is defined as the dose that prevents or provides substantial relief from nausea and/or vomiting or relieves the symptoms of other diseases or disorders.

A proposed dose of the active ingredient for administration in man (of approximately 70 kg body weight) is 0.05 to 50 mg, preferably 0.1 to 15 mg of active ingredient per unit dose which could be administered, for example, 1 to 4 times per day. The dose could be predetermined by testing in the human model of emesis which uses syrup of Ipecac as the emetic agent (Minton, N. et al., 1993, Clin. Pharmacol. Ther. 54:53–57). This model has shown good correlation between effective dose to protect against ipecac-induced vomiting and the effective dose to protect against vomiting induced by chemotherapeutic agents. The dose will depend on the route of administration and the body weight of the patient. It will be appreciated that it may be necessary to make routine variations to the dosage depending on the age and the weight of the patient as well as the severity of the condition to be treated.

The pharmaceutical composition containing the active ingredient according to this invention may be used prophylactically and references in this specification to treatment include prophylactic treatment as well as alleviation of acute symtoms.

The pharmaceutical composition containing the active ingredient according to this invention may be used in combination with other antiemetic agents such as but not limited to ondansetron (Zofran™, Glaxo-Welcome), granisetron (Kytril™, Smith-Kline Beecham) or tropisetron (Navoban™, Sandoz).

It should be understood that various changes and modifications to the presently preferred embodiments described herein will be apparent to those skilled in the art. Such changes and modifications can be made without departing from the spirit and the scope of the present invention and without diminishing its attendant advantages. It is therefore intended that such changes and modifications be covered by the appended claims.

I claim:

1. A method of treatment of a disease or a disorder which can be ameliorated by antagonism of the 5-HT3 receptor which comprises administering to a human or an animal in need thereof an effective amount to relieve the symptoms of said disease or said disorder, of a compound selected from a group comprising estrone, delta-8-estrone, 2-OH estrone, 4-OH estrone, equilin, equilenin clomestrone, or estropipate including pharmaceutical acceptable salts thereof.

2. A method according to claim 1 wherein said disorder is nausea and/or vomiting.

3. A method according to claim 2 wherein the nausea and/or vomiting is caused by a chemotherapeutic agent.

4. A method according to claim 3 wherein said chemotherapeutic agent is cisplatin.

5. A method according to claim 2 wherein the nausea and/or vomiting is caused by radiotherapy.

6. A method according to claim 2 wherein the nausea and/or vomiting is caused by a general anesthetic agent.

7. A method according to claim 2 wherein said compound or pharmaceutically acceptable salt thereof is contained in a pharmaceutical composition.

8. A method according to claim 7 wherein said pharmaceutical composition is administered by a route selected from the group including oral, intramuscular, intravenous and transdermal administration.

9. A method of treatment to prevent or to provide substantial relief from nausea and/or vomiting which comprises administering to a human or an animal in need thereof an effective amount to prevent or to provide substantial relief from nausea and/or vomiting, of estrone or a pharmaceutically acceptable salt thereof.

10. A method according to claim 9 wherein the need arises from administering for the treatment of cancer or other diseases a chemotherapeutic agent.

11. A method according to claim 10 wherein said chemotherapeutic agent is cisplatin.

12. A method according to claim 9 wherein the need arises from administering for the treatment of cancer or other diseases radiation.

13. A method according to claim 9 wherein the need arises from administering for the purpose of surgery a general anesthetic agent.

14. A method according to claim 9 wherein a metabolic precursor of estrone is administered.

15. A method according to claim 14 wherein said metabolic precursor is estradiol.

16. A method according to claim 9 wherein estrone or a pharmaceutically acceptable salt thereof is contained in a composition.

17. A method according to claim 16 wherein said pharmaceutical composition is administered by a route selected from the group including oral, intramuscular, intravenous and transdermal administration.

18. A method of treatment to prevent or to provide substantial relief from nausea and/or vomiting which comprises administering to a human or an animal in need thereof an effective amount, to prevent or to provide substantial relief from nausea and/or vomiting, of a pharmaceutical composition comprising a compound selected from a group comprising estrone delta-8-estrone, 2-OH estrone, 4-OH-estrone, equilin, equilenin clomestrone, or estropipate or a pharmaceutically acceptable salt of said compound.

19. A method according to claim 18 wherein the need arises from administration of a chemotherapeutic agent, radiation or a general anesthetic agent.

20. A method according to claim 18 wherein said compound or pharmaceutically acceptable salt thereof is contained in a pharmaceutical composition.

21. A method according to claim 20 wherein said pharmaceutical composition is administered by a route selected from the group including oral, intramuscular, intravenous and transdermal administration.

* * * * *